(12) United States Patent
Li et al.

(10) Patent No.: US 11,884,952 B2
(45) Date of Patent: Jan. 30, 2024

(54) DAPTOMYCIN-PRODUCING STREPTOMYCES STRAIN AND USE THEREOF

(71) Applicant: ZHEJIANG UNIVERSITY, Hangzhou (CN)

(72) Inventors: Yongquan Li, Hangzhou (CN); Jiaole Fang, Hangzhou (CN); Xuming Mao, Hangzhou (CN); Xinai Chen, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 111 days.

(21) Appl. No.: 17/042,173

(22) PCT Filed: Apr. 21, 2020

(86) PCT No.: PCT/CN2020/085791
§ 371 (c)(1),
(2) Date: Sep. 27, 2020

(87) PCT Pub. No.: WO2021/000637
PCT Pub. Date: Jan. 7, 2021

(65) Prior Publication Data
US 2023/0118242 A1    Apr. 20, 2023

(30) Foreign Application Priority Data
Jul. 1, 2019 (CN) .......................... 201910585448.7

(51) Int. Cl.
*C12P 21/02* (2006.01)
*C12N 1/20* (2006.01)
*C12R 1/545* (2006.01)

(52) U.S. Cl.
CPC .............. *C12P 21/02* (2013.01); *C12N 1/205* (2021.05); *C12R 2001/545* (2021.05)

(58) Field of Classification Search
CPC .................................................... C12P 21/02
See application file for complete search history.

(56) References Cited

U.S. PATENT DOCUMENTS

2014/0147425 A1 * 5/2014 Henn .................... A23L 33/135
424/93.4

FOREIGN PATENT DOCUMENTS

| CN | 101899410 A | 12/2010 | |
|---|---|---|---|
| CN | 102399706 A | 4/2012 | |
| CN | 110343638 A | 10/2019 | |
| EP | 2390341 A1 * | 11/2011 | ............. C12N 1/205 |
| WO | 2015093839 A1 | 6/2015 | |
| WO | WO-2016080665 A1 * | 5/2016 | ............... C12P 1/04 |
| WO | 2018045004 A1 | 3/2018 | |

OTHER PUBLICATIONS

Miao et al. "Daptomycin biosynthesis in Streptomyces roseosporus: cloning and analysis of the gene cluster and revision of peptide stereochemistry" Microbiology (2005), 151, 1507-1523 (Year: 2005).*
International Search Report (PCT/CN2020/085791); dated Jul. 27, 2020.
"Advances in daptomycin biosynthesis" (Oct. 20, 2013) [Xie Xiang-Mao et al.].

* cited by examiner

*Primary Examiner* — Thane Underdahl
(74) *Attorney, Agent, or Firm* — W&G Law Group

(57) ABSTRACT

The present invention provides a novel daptomycin-producing *Streptomyces* strain and use thereof, the strain is a subspecies of *streptomyces griseus*, named *Streptomyces griseus* L340, and the preservation number is CGMCC17921. The genetic character and fermentation unit of the strain provided by the present invention are relatively stable, the culture and fermentation conditions are suitable for industrial production of daptomycin, and the interference of pigment in later separation and purification is eliminated. The secondary metabolite daptomycin is obtained through fermentation of the *Streptomyces* provided by the present invention, which has the advantages of no interference of pigment accumulation, cleaner metabolic spectrum and thus is obviously superior in later separation and purification.

5 Claims, 3 Drawing Sheets
Specification includes a Sequence Listing.

SEQUENCE LISTING

<160> NUMBER OF SEQ ID NOS: 1

<210> SEQ ID NO 1
<211> LENGTH: 1531
<212> TYPE: DNA
<213> ORGANISM: Streptomyces griseus L340

-continued

<400> SEQUENCE: 1

```
aaaggaggtg atccagccgc accttccggt acggctacct tgttacgact tcgtcccaat        60
cgccagtccc accttcgaca gctccctccc acaaggggtt gggccaccgg cttcgggtgt       120
taccgacttt cgtgacgtga cgggcggtgt gtacaaggcc cgggaacgta ttcaccgcag       180
caatgctgat ctgcgattac tagcaactcc gacttcatgg ggtcgagttg cagaccccaa       240
tccgaactga gaccggcttt ttgagattcg ctccgcctcg cggcatcgca gctcattgta       300
ccggccattg tagcacgtgt gcagcccaag acataagggg catgatgact tgacgtcgtc       360
cccaccttcc tccgagttga ccccggcagt ctcctgtgag tccccatcac cccgaagggc       420
atgctggcaa cacagaacaa gggttgcgct cgttgcggga cttaacccaa catctcacga       480
cacgagctga cgacaccat gcaccacctg tataccgacc acaagggggg caccatctct       540
gatgctttcc ggtatatgtc aagccttggt aaggttcttc gcgttgcgtc gaattaagcc       600
acatgctccg ctgcttgtgc gggccccgt caattccttt gagttttagc cttgcggccg       660
tactccccag gcggggaact taatgcgtta gctgcggcac cgacgacgtg gaatgtcgcc       720
aacacctagt tcccaacgtt tacggcgtgg actaccaggg tatctaatcc tgttcgctcc       780
ccacgctttc gctcctcagc gtcagtaatg gcccagagat ccgccttcgc caccggtgtt       840
cctcctgata tctgcgcatt tcaccgctac accaggaatt ccgatctccc ctaccacact       900
ctagctagcc cgtatcgaat gcagacccgg ggttaagccc cgggctttca catccgacgt       960
gacaagccgc ctacgagctc tttacgccca ataattccgg acaacgcttg cgccctacgt      1020
attaccgcgg ctgctggcac gtagttagcc ggcgcttctt ctgcaggtac cgtcactttc      1080
gcttcttccc tgctgaaaga ggtttacaac ccgaaggccg tcatccctca cgcggcgtcg      1140
ctgcatcagg ctttcgccca ttgtgcaata ttccccactg ctgcctcccg taggagtctg      1200
ggccgtgtct cagtcccagt gtggccggtc gccctctcag gccggctacc cgtcgtcgcc      1260
ttggtaggcc attaccccac caacaagctg ataggccgcg ggctcatcct tcaccgccgg      1320
agctttcaac cccgtcccat gcgggacaga gtgttatccg gtattagacc ccgtttccag      1380
ggcttgtccc agagtgaagg gcagattgcc cacgtgttac tcacccgttc gccactaatc      1440
caccaccgaa gtgatttcat cgttcgactt gcatgtgtta agcacgccgc cagcgttcgt      1500
cctgagccag gatcaaactc tccgtgaatg t                                      1531
```

DAPTOMYCIN-PRODUCING STREPTOMYCES STRAIN AND USE THEREOF

CROSS-REFERENCE TO RELATED APPLICATIONS

This is the United States national phase of International Patent Application No. PCT/CN2020/085791, filed on Apr. 21, 2020, which claims priority of Chinese patent application No. 2019105854487 filed on Jul. 1, 2019, the entire contents of which are incorporated herein by reference in their entireties.

REFERENCE TO DEPOSIT CERTIFICATE

The present application is being filed along with a deposit certificate of *Streptomyces griseus* L340, which is provided as a file entitled "DF202791US_deposit certificate", in which the deposited material *Streptomyces griseus* L340 is deposited by the applicant ZHEJIANG UNIVERSITY addressed in Hangzhou City, Zhejiang Province, PRC, on Jun. 12, 2019, with a deposit (accession) number of "CGMCC No. 17921", and a taxonomic name of "Streptomyces griseus". The information in the deposit certificate is incorporated herein by reference in its entirety. In addition, the deposited material *Streptomyces griseus* L340 has been accepted for deposit by China General Microbiological Culture Collection Center (CGMCC) under the Budapest Treaty on the International Recognition of the Deposit of Microorganisms for the purpose of Patent Procedure and that all restrictions on the availability to the public of the material so deposited will be irrevocably removed upon the granting of a patent.

TECHNICAL FIELD

The present invention belongs to the field of microorganisms and relates to a novel daptomycin-producing *Streptomyces* strain and use thereof.

BACKGROUND

Daptomycin is a kind of cycloaliphatic peptide antibiotic with a brand-new structure extracted from the fermentation broth of *S. roseosporus*. It was discovered by Eli Lilly and Company of the United States in 1980s and successfully developed by Cubist Pharmaceutical Company in 1997. It not only has a novel chemical structure, but also has a different mode of action from any approved antibiotic: it disturbs the transport of amino acids by cell membrane, thereby hindering the biosynthesis of peptidoglycan in bacterial cell walls and changing the nature of plasma membrane. In addition to being able to act on most clinically related Gram-positive bacteria, it is more important that daptomycin has a strong activity against isolated strains which have shown methicillin, vancomycin and linezolid resistance in vitro.

In September 2003, the US Food and Drug Administration approved daptomycin for the treatment of severe skin infections for the first time, and in March 2006, it was approved for infectious diseases.

In January 2006, it was approved by the European Commission to treat complicated skin and soft tissue infections caused by some Gram-positive bacteria.

On Sep. 6, 2007, Cubist Pharmaceutical Company announced that the European Union had approved its antibacterial drug daptomycin for injection (Cubicin) to treat right heart infective endocarditis caused by *Staphylococcus aureus* and *Staphylococcus aureus* bacteremia related to right heart infective endocarditis or complicated skin and soft tissue infection.

For a long time, *S. roseosporus* was used in the fermentation production of daptomycin, whose secondary metabolites were complex and the by-product pigment accumulated a lot, which made it difficult to separate and purify daptomycin in the later stage.

SUMMARY

The present invention provides a novel daptomycin-producing *Streptomyces* strain. Compare with the traditional daptomycin-producing bacteria *S. roseosporus*, the novel daptomycin-producing strain provided by the invention has the great advantage that pigment substances are not produced in the process of subculture and fermentation, thereby reducing the difficulty for subsequent separation and purification operations.

The *Streptomyces* strain provided by the present invention is named as *Streptomyces griseus* L340. The 16S rDNA sequence (SEQ ID No.1) of the genome of this strain is highly homologous to streptomyces griseus, but its phenotype is quite different. The strain provided by the present invention is preserved in China General Microbiological Culture Collection Center with the preservation date of Jun. 12, 2019, and the preservation number CGMCC No. 17921.

The method for culturing the Streptomyces strain provided by the present invention is as below:
(1) solid culture: inoculating the strain on an agarslantculture-medium, and culturing in an incubator at 30° C. for 5-8 days;
(2) liquid culture: cutting spores from the agarslantculture-medium and inoculating into a seed broth, culturing on a shaker with a rotation speed of 250 rpm at 30° C. for 36 hours, then inoculating a transfer amount of 4% into a fermentation medium, and culturing on a shaker with a rotation speed of 250 rpm at 30° C. for 4-6 days.

The medium (R5) used in the solid culture: the agarslantculture-medium for *Streptomyces* is a R5 medium, and each liter of the medium contains 103 g of sucrose, 10 g of glucose, 5 g of yeast extract, 0.1 g of casein hydrolysate, 0.25 g of $K_2SO_4$, 10.12 g of $MgCl_2 \cdot 6H_2O$, 2 mL of a trace element solution, 5.73 g of TES buffer, 0.3 g of L-proline, which are diluted by water to a volume of 1 L (22 g of agar is added to a solid medium), which is sterilized at 115° C. for 25 min. After sterilization, the following solutions are added in sequentce: 10 mL of 5% $KH_2PO_4$, 4 mL of 5 M $CaCl_2 \cdot 2H_2O$, 700 μL of 10 M NaOH, which are shaken well, poured onto a flat plate and solidified for later use. A trace element storage solution: 40 mg of $ZnCl_2$, 200 mg of $FeCl_3 \cdot 6H_2O$, 10 mg of $CuCl_2 \cdot 2H_2O$, 10 mg of $MnCl \cdot 4H_2O$, 10 mg of $Na_2B_4O_7 \cdot 10H_2O$, and 10 mg of $(NH_4)Mo_7O_{24} \cdot 4H_2O$, to which water is added to a volume of 1 L for later use.

The seed broth (TSB, Trypticase Soy Broth medium): TSB 2%, PEG 6000 5%, which are diluted by water to a volume of 1 L, wherein the percentages are percentages by mass. The medium is sterilized at 115° C. for 25 min for later use.

The fermentation medium (YEME(4%), Yeast Extract, Malt Extract, Tryptone, 4% glucose, a yeast malt medium): 0.3% yeast extract, 0.3% malt extract, 0.5% tryptone, and 4% glucose, which are diluted by water to a volume of 1 L, wherein the percentages are percentages by mass. The medium is sterilized at 115° C. for 25 min for later use.

Another object of the invention is to provide a production method of the *Streptomyces griseus* L340 in producing daptomycin. The Streptomyces strain from soil provided by the invention can obtain the secondary metabolite daptomycin through fermentation, and has the advantages of no interference of pigment accumulation, cleaner metabolic spectrum, and thus is obviously superior in later separation and purification. The fermentation process for producing daptomycin by *Streptomyces* is as follows:

(1) cutting spores from a agarslantculture-medium, inoculating the spores into a seed broth, and culturing on a shaker with a rotation speed of 250 rpm at 30° C. for 36 hours until a bacterial liquid is sticky and granular;

(2) harvesting 4% by volume of the bacterial liquid from the seed broth, inoculating into the fermentation medium, and culturing on a shaker with a rotation speed of 250 rpm at 30° C.; and after 48 hours, supplementarily feeding decanoic acid in 0.1% by volume of the medium every 12 hours, wherein the decanoic acid supplementary feed is prepared by mixing decanoic acid and methyl oleate in a volume ratio of 1:1; and (3) after 144 hours, treating the fermentation broth with methanol of equal volume, and subjecting a supernatant obtained after centrifugation to subsequent separation and purification to obtain the daptomycin.

The above-mentioned agarslantculture-medium, seed broth and fermentation medium are defined as in the above-mentioned *Streptomyces* culture method.

The main advantages of the present invention are:

(1) Compared with the traditional daptomycin-producing strain *Streptomyces roseosporus*, this *Streptomyces* does not produce pigments during subculture and fermentation. Because pigments usually need extra steps to be treated in the separation and purification, the separation and purification yield of final product samples often decreases, and even the samples are impure. According to the *Streptomyces* isolated and purified from the soil, after the strain is cultured in the R5 agar medium for 5-8 days, the substrate mycelium and aerial mycelium develop well, the spores are white, and no colored substances are produced in the culture process. The strain grows well in a YEME liquid medium, does not produce colored substances, and its metabolic spectrum is relatively simple. Therefore, the pigment-free strain of the present invention has obvious advantages in the later stage separation and purification in industrial production.

(2) Because no pigment substances are produced, the *Streptomyces* can effectively reduce the consumption of various precursor substances in the fermentation process during subculture and fermentation, thereby reducing the consumption level of carbon and nitrogen sources in the medium, thus reducing the amount of supplementary materials in industrial culture and making industrial production more efficient.

(3) There is no interference of pigments, which makes the detection of related metabolites and microscopic examination of bacteria more convenient and direct, thus reducing the working level in the industrial fermentation process.

(4) The pigment-free strain can be used as a good starting strain, and the phenotypic changes can be clearly observed in the subsequent mutation and screening of strains. Because many secondary metabolites have visible light absorption, they can also be used as heterologous expression hosts for genetic manipulation.

BRIEF DESCRIPTION OF DRAWINGS

FIG. 3-B shows the supernatant and mycelial morphology of the fermentation liquid after centrifugation. It can be seen that a large amount of red pigment is produced in the fermentation process of *Streptomyces roseosporus*, while the present invention declares that no pigment substance is produced in either the mycelium or the supernatant of *Streptomyces* (the light yellow color of the supernatant is the background color of the medium).

DESCRIPTION OF EMBODIMENTS

The present invention will be further explained with reference to drawings and examples.

The experimental methods in the following examples are all conventional methods, unless otherwise specified.

The medium used in the examples:

A slant R5 agar medium: each liter of the medium contains 103 g of sucrose, 10 g of glucose, 5 g of yeast extract, 0.1 g of casein hydrolysate, 0.25 g of $K_2SO_4$, 10.12 g of $MgCl_2 \cdot 6H_2O$, 2 mL of a trace element solution, 5.73 g of TES buffer, 0.3 g of L-proline, which are diluted by water to a volume of 1 L (22 g of agar is added to a solid medium), which is sterilized at 115° C. for 25 min. After sterilization, the following solutions are added in turn: 10 mL of 5% $KH_2PO_4$, 4 mL of 5M $CaCl_2 \cdot 2H_2O$, 700 μL of 10M NaOH, which are shaken well, poured onto the plate and solidified for later use. A trace element storage solution: 40 mg of $ZnCl_2$, 200 mg of $FeCl_3 \cdot 6H_2O$, 10 mg of $CuCl_2 \cdot 2H_2O$, 10 mg of $MnCl.4H_2O$, 10 mg of $Na_2B_4O_7 \cdot 10H_2O$ and 10 mg of $(NH_4)_6Mo_7O_{24} \cdot 4H_2O$, to which water is added to a volume of 1 L for later use.

A seed broth (TSB): TSB 2%, PEG 6000 5%, which are diluted by water to a volume of 1 L; wherein, the percentages are by mass. The medium is sterilized at 115° C. for 25 min for later use.

A fermentation medium (YEME): 0.3% yeast extract, 0.3% malt extract, 0.5% tryptone, and 4% glucose, which are diluted by water to a volume of 1 L; wherein, the percentages are by mass. The medium is sterilized at 115° C. for 25 min for later use.

EXAMPLE 1

The present invention provides a novel daptomycin-producing *Streptomyces* strain. Compare with the traditional daptomycin-producing bacteria *Streptomyces roseosporus*, the novel daptomycin-producing strain provided by the invention has the great advantage that pigment substances are not produced in the process of subculture and fermentation, thereby reducing the difficulty for subsequent separation and purification operations. The strain provided by the present invention is preserved in China General Microbiological Culture Collection Center with the preservation date of Jun. 12, 2019, and the preservation number of CGMCC17921.

Figure 1:
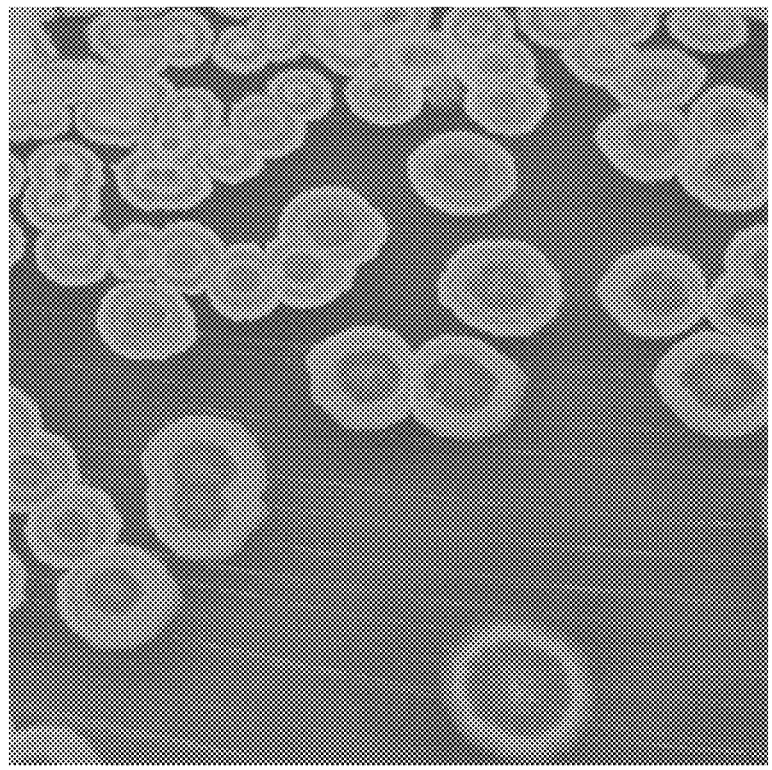
FIG. 1: a monoclonal morphology of *Streptomyces* colonies cultured on a R5 plate medium for 7 days, wherein the monoclonal irregularly round as a whole, with a slightly convex surface and radial cracks; the spores are gray-white and easy to fall off, which are concentrated at the edge of the monoclonal.
Figure 2:
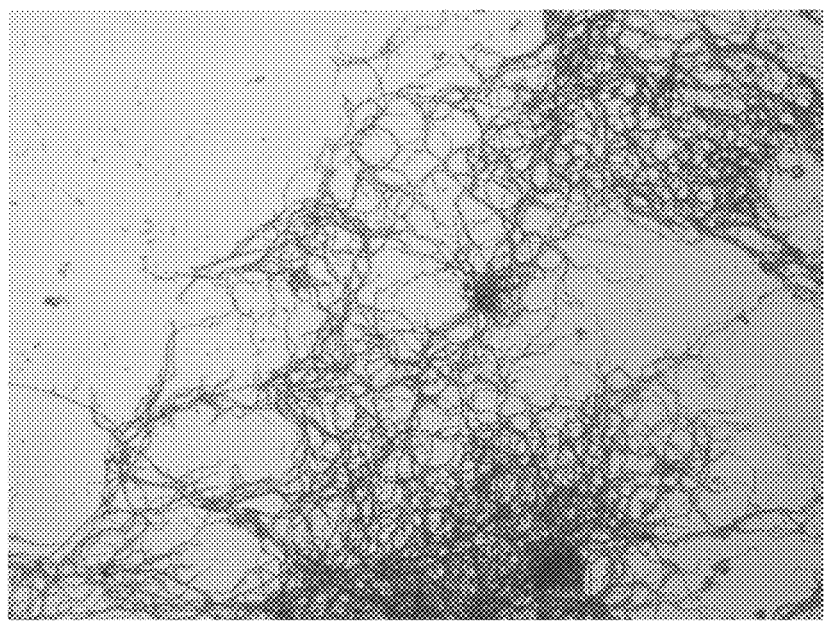
FIG. 2: the morphology of bacteria in *Streptomyces* fermentation broth provided by the present invention.

The apparent characteristics in different media are shown in Table 1, in which the colony morphology on a R5 medium is shown in FIG. 1, and the mycelium morphology on a YEME medium is shown in FIG. 2. See Table 2 for physiological and biochemical characteristics of L10.

Figure 4:
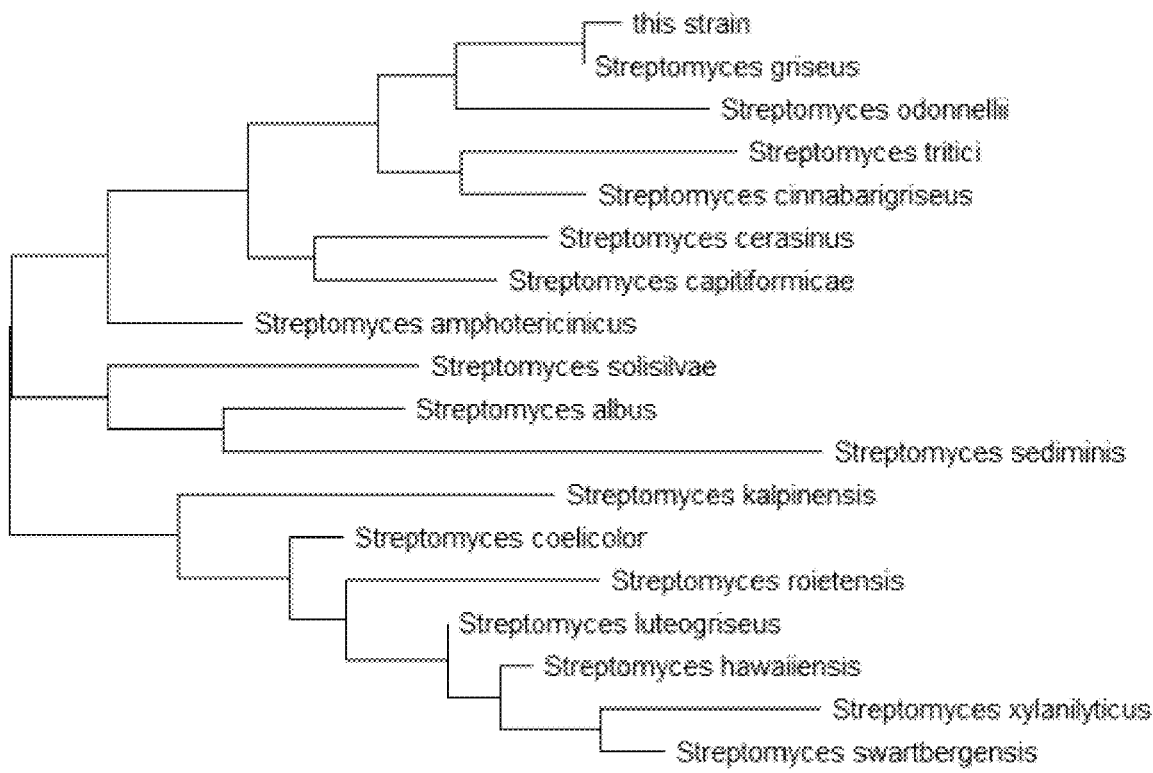
FIG. 4: the phylogenetic tree of the 16s rDNA sequence shows that the homology with *streptomyces griseus* is 99.41%, and the homology with *Streptomyces coelicolor* is 96.9%, which indicates that the present *Streptomyces* has similar genetic relationship with *streptomyces griseus*.

Compared with other 17 *Streptomyces* strains (see FIG. 4 for the phylogenetic tree), the sequencing results of 16srDNA of *Streptomyces* declared by the present invention show that the homology with *streptomyces griseus* is 99.41%, and the homology with *Streptomyces coelicolor* is 96.9%, indicating that *Streptomyces* has similar genetic relationship with *streptomyces griseus*.

TABLE 1

Cultural characteristics of strains:

| Medium | Soluble pigment | Aerial mycelium | Color of the back side of the medium |
|---|---|---|---|
| YEME | none | white | yellowish |
| ISP4 | none | white | yellowish |
| MM | grey | white | white |
| R5 | none | white | yellowish |

TABLE 2

Physiological and biochemical characteristics of strains:

| Characteristics | Results |
|---|---|
| pH range for growth | |
| pH < 4 | − |
| pH = 5-11 | + |
| pH = 12 | W |
| NaCl tolerance | |
| 3% NaCl | + |
| 5% NaCl | W |
| 7% NaCl | − |
| Growth temperature | |
| 30° C. | + |
| 37° C. | − |
| Melanin production | − |
| Milk coagulation | + |
| Starch hydrolysis | + |
| Gelatin liquefaction | + |

TABLE 2-continued

Physiological and biochemical characteristics of strains:

| Characteristics | Results |
|---|---|
| Used carbon source | |
| D-glucose | + |
| D-fructose | + |
| Maltose | + |
| Sucrose | + |
| Glycerol | + |
| Inositol | + |
| D-mannitol | + |
| L-arabinose | − |
| D-xylose | − |
| L-rhamnose | − |
| Sodium acetate | − |
| Raffinose | − |
| Sorbitol | − |

Note:
"W" indicates a weak positive result, "+" indicates a positive result and "−" indicates a negative result

EXAMPLE 2

The method for culturing the daptomycin-producing *Streptomyces* strain is as below:

(1) solid culture: inoculating the strain on a agarslantculture-medium, and culturing the strain in an incubator at 30° C. for 5-8 days;

(2) liquid culture: inoculating the strain into a seed broth, culturing the strain on a shaker with a rotation speed of 250 rpm at 30° C. for 36 hours, then inoculating the strain into a fermentation medium based on a transfer amount of 4%, and culturing the strain on a shaker with a rotation speed of 250 rpm at 30° C. for 4-6 days; feeding 0.1% by volume of decanoic acid every 12 hours after 48 hours.

EXAMPLE 3

Figure 3:
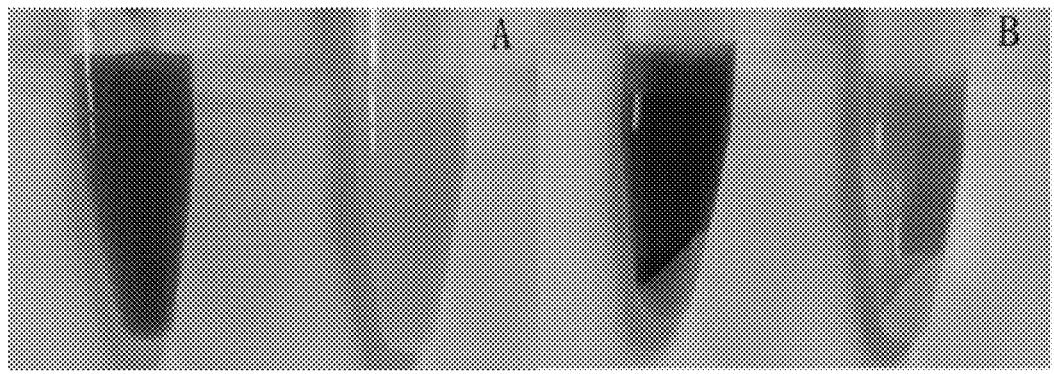
FIG. 3: comparison of fermentation broth morphology between the *Streptomyces* and the traditional daptomycin-producing strain, i.e., *Streptomyces roseosporus*, in a traditional daptomycin-producing medium, a YEME(4%) liquid medium; wherein, FIG. 3-A shows the broth morphology after 144 h of fermentation, red representing *Streptomyces roseosporus*, and white representing *Streptomyces* of the present application, the right being the same.
Figure 5:
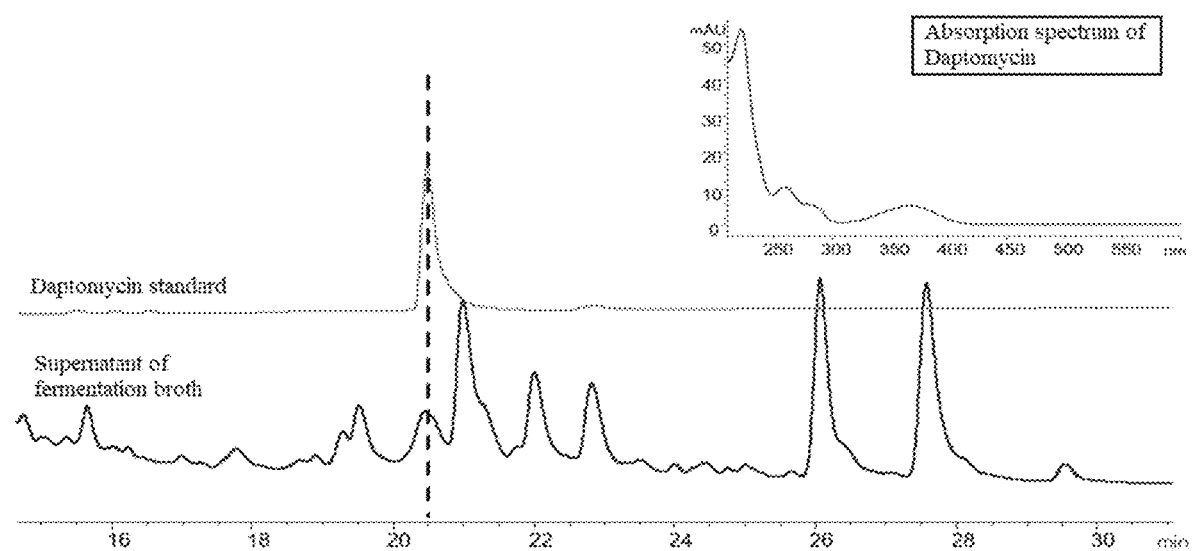
FIG. 5: the metabolic spectrum of the fermentation broth of the *Streptomyces* of the present application in the YEME (4%) fermentation experiment after 144 hours detected by HPLC.

Shake flask fermentation was carried out according to Example 2, and samples were taken after 144 h hours. The color of the bacterial liquid at this time is shown in FIG. 3, which shows that compared with traditional daptomycin-producing strains, pigment is completely eliminated, which is beneficial to subsequent separation. Methanol was added in a volume ratio of 1:1, and the supernatant was identified by HPLC (high performance liquid chromatography) after shaking centrifugation. As shown in FIG. 5, daptomycin could be detected before and after 21 min, and the yield calculated by the standard curve of daptomycin was 31.5 mg/L.

The HPLC detection method is: HPLC chromatographic column: XDB-C18

Phase A: $H_2O$+0.05% formic acid; phase B: acetonitrile +0.05% formic acid; Gradient of phase B is 5%-100%, 35 min.

The absorption peak of daptomycin can be seen at 21 min.

What is claimed is:

1. A novel daptomycin-producing *Streptomyces* strain, wherein the *Streptomyces* strain is classified and named as *Streptomyces griseus* L340 preserved in China General Microbiological Culture Collection Center with a preservation date of Jun. 12, 2019 and a preservation number of CGMCC No. 17921, and the strain is kept in a media with a buffer to maintain the pH 5-11.

2. A method for culturing the Streptomyces strain according to claim 1, comprising the following steps:
   (1) solid culture: inoculating the strain on an agarslantculture-medium, and culturing in an incubator at 30° C. for 5-8 days; and
   (2) liquid culture: cutting spores from the agarslantculture-medium and inoculating into a seed broth, culturing on a shaker with a rotation speed of 250 rpm at 30° C. for 36 hours, then inoculating a transfer amount of 4% into a fermentation medium, and culturing on a shaker with a rotation speed of 250 rpm at 30° C. for 4-6 days.

3. The method according to claim 2, wherein the agarslantculture-medium in the step (1) is a R5 medium, each liter of medium which contains 103 g of sucrose, 10 g of glucose, 5 g of yeast extract, 0.1 g of casein hydrolysate, 0.25 g of $K_2SO_4$, 10.12 g of $MgCl_2 \cdot 6H_2O$, 2 mL of a trace element solution, 5.73 g of TES buffer, and 0.3 g of proline, which are diluted by water to a volume of 1 L, and 22 g of agar is added to a solid medium;
   in the step (2), the seed broth is a Trypticase Soy Broth medium: TSB 2%, PEG 6000 5%, which are diluted by water to a volume of 1 L, wherein the percentages are percentages by mass; and
   the fermentation medium in the step (2) is a yeast malt medium: 0.3% yeast extract, 0.3% malt extract, 0.5% tryptone, and 4% glucose, which are diluted to a volume of 1 L.

4. A production method of daptomycin using the *Streptomyces griseus* L340 according to claim 1, comprising the following steps:

(1) cutting spores from an agarslantculture-medium, inoculating the spores into a seed broth, and culturing on a shaker with a rotation speed of 250 rpm at 30° C. for 36 hours until a bacterial liquid is sticky and granular;
(2) harvesting 4% by volume of the bacterial liquid from the seed broth, inoculating into the fermentation medium, and culturing on a shaker with a rotation speed of 250 rpm at 30° C.; and after 48 hours, feeding decanoic acid in 0.1% by volume of the fermentation medium every 12 hours;
(3) after 144 hours, treating the fermentation broth with methanol of equal volume, and subjecting a supernatant obtained after centrifugation to subsequent separation and purification to obtain the daptomycin.

5. The production method according to claim 4, wherein, definitions of the agarslantculture-medium, the seed broth and the fermentation medium are the same as in claim 3.

\* \* \* \* \*